US008913114B2

(12) United States Patent
Yoshino

(10) Patent No.: US 8,913,114 B2
(45) Date of Patent: Dec. 16, 2014

(54) CALIBRATION TOOL FOR SCANNING ENDOSCOPE

(71) Applicant: Olympus Medical Systems Corp., Tokyo (JP)

(72) Inventor: Masahiro Yoshino, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/947,471

(22) Filed: Jul. 22, 2013

(65) Prior Publication Data

US 2014/0022365 A1 Jan. 23, 2014

Related U.S. Application Data

(63) Continuation of application No. PCT/JP2013/059240, filed on Mar. 28, 2013.

(30) Foreign Application Priority Data

May 23, 2012 (JP) ................................ 2012-117769

(51) Int. Cl.

| | |
|---|---|
| ***A61B 1/00*** | (2006.01) |
| ***H04N 17/00*** | (2006.01) |
| ***G02B 23/26*** | (2006.01) |
| ***G02B 23/24*** | (2006.01) |

(52) U.S. Cl.

CPC .............. *H04N 17/002* (2013.01); *G02B 23/26* (2013.01); *G02B 23/2423* (2013.01); *G02B 23/2476* (2013.01); *A61B 1/00057* (2013.01); *A61B 1/0011* (2013.01); *A61B 1/00172* (2013.01)

USPC ........................................................... 348/65

(58) Field of Classification Search

USPC ........................................................... 348/65

See application file for complete search history.

(56) References Cited

U.S. PATENT DOCUMENTS

2008/0094631 A1* 4/2008 Jung et al. ..................... 356/419
2008/0165360 A1 7/2008 Johnston
2010/0048993 A1 2/2010 Shidara
2013/0003131 A1 1/2013 Johnston

FOREIGN PATENT DOCUMENTS

JP 2010-046276 A 3/2010
JP 2010-515947 A 5/2010
JP 2011-067650 A 4/2011
WO WO 2008/085186 A1 7/2008

* cited by examiner

*Primary Examiner* — Sath V Perungavoor
*Assistant Examiner* — Jeffery Williams
(74) *Attorney, Agent, or Firm* — Scully, Scott, Murphy & Presser, P.C.

(57) ABSTRACT

A calibration tool for a scanning endoscope includes: an abutment portion that is in contact with and abuts an illumination window provided in a distal end face of an insertion portion of a scanning endoscope and is configured to be in contact with a region of the illumination window other than a region in which an illuminating light beam applied from the illumination window is scanned; and a chart with a calibration pattern drawn thereon, the calibration pattern being provided for calibrating a scan pattern of the illuminating light, the chart being arranged parallel to the distal end face with a predetermined distance from a surface of the illumination window positioned as a result of the illumination window coming into contact with the abutment portion, according to a size of the calibration pattern, whereby image calibration of the scanning endoscope can accurately be performed with a simple configuration.

7 Claims, 14 Drawing Sheets

LIGHT SOURCE UNIT
LIGHT SOURCE (R)
LIGHT SOURCE (G)
LIGHT SOURCE (B)
MULTIPLEXER
DRIVER UNIT
SIGNAL GENERATOR
D/A CONVERTER
D/A CONVERTER
AMPLIFIER
DETECTION UNIT
DEMULTIPLEXER
DETECTOR (R)
DETECTOR (G)
DETECTOR (B)
A/D CONVERTER
A/D CONVERTER
A/D CONVERTER
CONTROLLER
MEMORY
MEMORY
MONITOR
POWER SUPPLY
1
2
3
4
11
12
12a
13
13a
13b
14
15
16
16
17
21
22
23
24
25
26
31a
31b
31c
32
33
34a
34b
35
36
37a
37b
37c
38a
38b
38c (a) X-AXIS (b) Y-AXIS

CALIBRATION TOOL FOR SCANNING ENDOSCOPE

CROSS REFERENCE TO RELATED APPLICATION

This application is a continuation application of PCT/JP2013/059240 filed on Mar. 28, 2013 and claims benefit of Japanese Application No. 2012-117769 filed in Japan on May 23, 2012, the entire contents of which are incorporated herein by this reference.

BACKGROUND OF THE INVENTION

1. Field of the Invention

The present invention relates to a calibration tool for a scanning endoscope, which is used for a scanning endoscope that scans an optical fiber from which illuminating light is applied, detects return light to create an image, and performs calibration of a locus of a scan of light from the optical fiber in the scanning endoscope apparatus.

2. Description of the Related Art

As is known, there are electronic endoscopes that photoelectrically convert a subject image by means of an image pickup apparatus including a solid-state image pickup device such as a CCD or a CMOS and display an acquired image on a monitor. In recent years, as apparatuses that display an object image without using the technique of such solid-state image pickup device, endoscope apparatuses that scan a distal end of an illumination fiber, which guides light from a light source and receive return light from a subject via an optical fiber bundle arranged in the periphery of the illumination fiber, to create an image using a light intensity signal detected over time, have been known.

As an example of the technique of such endoscope apparatus that scans an optical fiber and acquires an image, Japanese Patent Application Laid-Open Publication No. 2010-515947 discloses a scanning beam apparatus. Patent Literature 1 above discloses a method for calibrating a scanning beam apparatus, the method including acquiring an image of a calibration pattern using the scanning beam apparatus, comparing the acquired image with a representation of the calibration pattern and calibrating the scanning beam apparatus based on the comparison, in order to improve distortion of the acquired image by enhancing the accuracy of estimation of the position of an illumination spot for each pixel point in a scan pattern, which depends on environmental variables, manufacturing variables, imperfect electronics, the sensitivity of the scanning fiber apparatus, which is an endoscope apparatus, around the resonance frequency, and/or other factors.

SUMMARY OF THE INVENTION

A calibration tool for a scanning endoscope according to an aspect of the present invention provides a calibration tool for a scanning endoscope, provided for calibrating an image acquired by a scanning endoscope that scans illuminating light and detects return light to create an image, the calibration tool including: an abutment portion that is in contact with and abuts an illumination window provided in a distal end face of an insertion portion of the scanning endoscope and is configured to be in contact with a region of the illumination window other than a region in which an illuminating light beam applied from the illumination window is scanned; and a chart with a calibration pattern drawn thereon, the calibration pattern being provided for calibrating a scan pattern of the illuminating light, the chart being arranged parallel to the distal end face with a predetermined distance from a surface of the illumination window positioned as a result of the illumination window coming into contact with the abutment portion, according to a size of the calibration pattern.

DETAILED DESCRIPTION OF THE PREFERRED EMBODIMENTS

An endoscope according to the present invention will be described below. Note that, in the below description, it should be noted that: the drawings based on the respective embodiments are schematics ones; e.g., a relationship between a thickness and a width of each part and ratios in thickness between the respective parts are different from actual ones; and the drawings may include parts with dimensional relationships and/or ratios mutually different among the drawings.

(Scanning Endoscope Apparatus)

Figure 1:
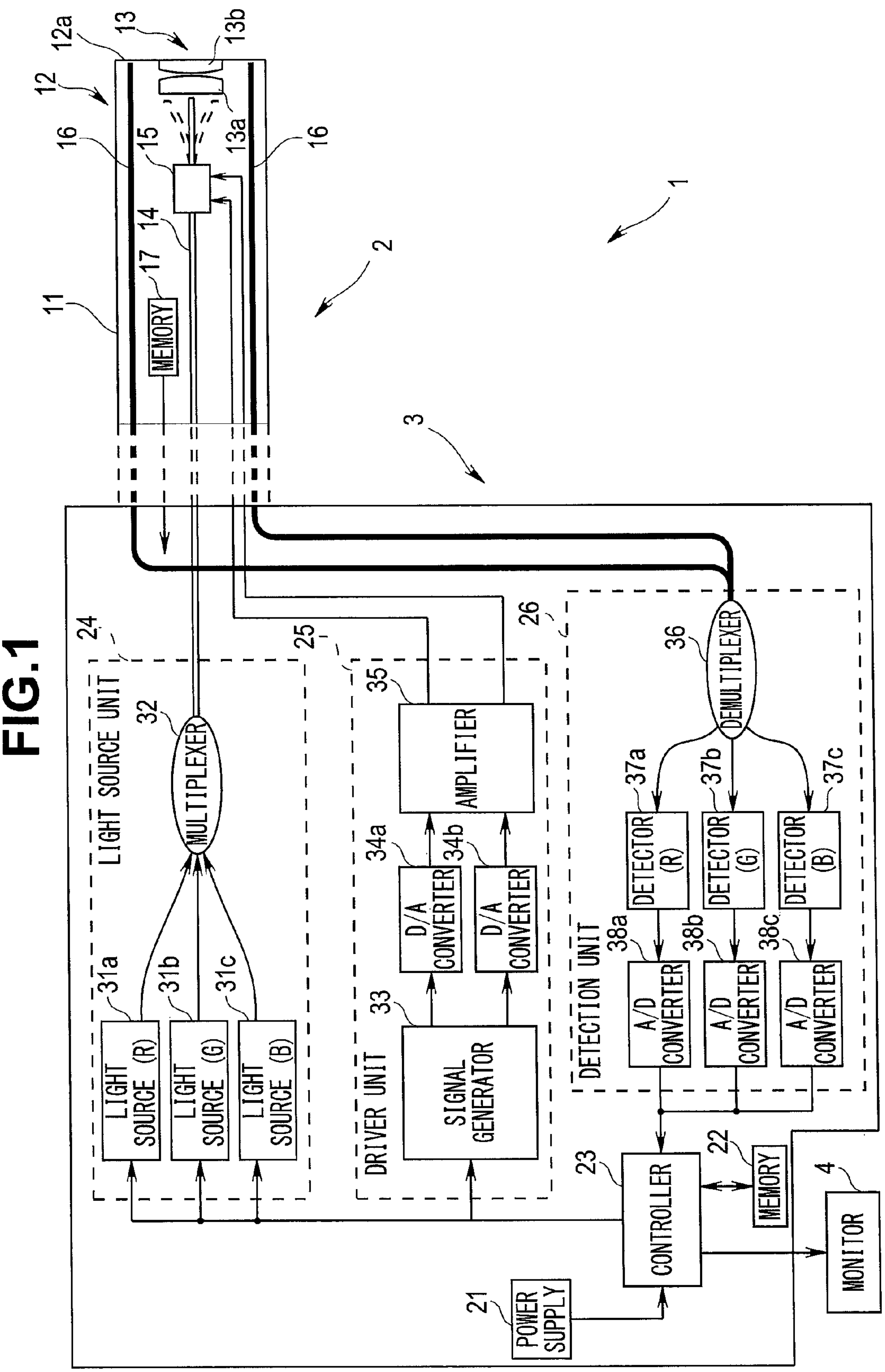
FIG. 1 is a diagram illustrating a configuration of an endoscope apparatus including a scanning endoscope.
Figure 2:
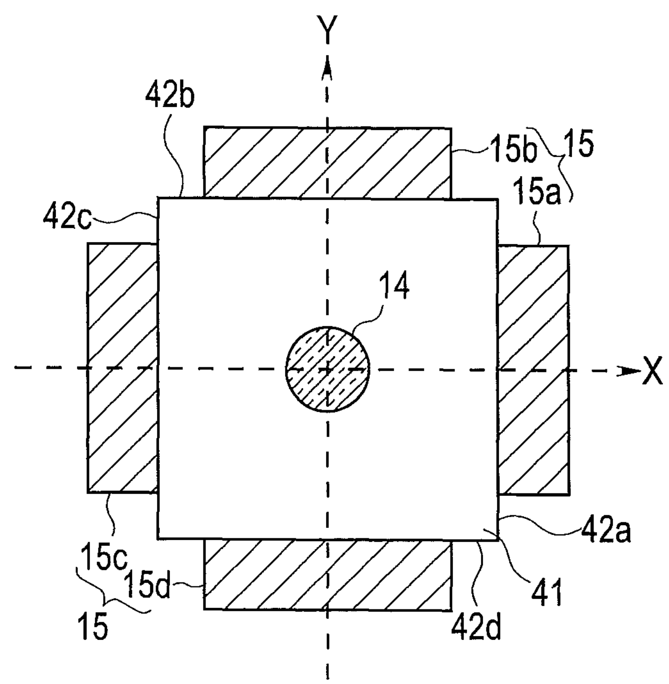
FIG. 2 is a diagram illustrating a configuration of an endoscope apparatus including a scanning endoscope: a cross-sectional view of an actuator in the scanning endoscope.

First, a configuration of an endoscope apparatus including a scanning endoscope will be described below with reference to FIGS. 1 and 2. FIG. 1 is a diagram illustrating a configuration of an endoscope apparatus including an endoscope according to a first embodiment, and FIG. 2 is a cross-sectional view of an actuator according to the first embodiment.

As illustrated in FIG. 1, an endoscope apparatus 1 includes a scanning endoscope (hereinafter simply referred to as "endoscope") 2 that applies illuminating light to a subject while scanning the illuminating light and acquires return light from the subject, a main body apparatus 3 connected to the endoscope 2, and a monitor 4 that displays a subject image acquired by the main body apparatus 3.

The endoscope 2 includes a tube body having a predetermined flexibility as a main body, and includes an elongated insertion portion 11 to be inserted into a living body. On the distal end side of the insertion portion 11, a distal end portion 12 is provided. Also, on the proximal end side of the insertion portion 11, a non-illustrated connector or the like is provided, and the endoscope 2 can detachably be connected to the main body apparatus 3 via the connector or the like.

At a distal end face 12*a* of the distal end portion 12, a distal end optical system 13 including illumination lenses 13*a* and 13*b* is provided. Note that the distal end optical system 13 is provided in such a manner that a center thereof coincides with a center of the distal end face 12*a* of the distal end portion 12.

Inside the insertion portion 11, an illumination fiber 14, which serves as an optical element that is inserted from the proximal end side to the distal end side and guides light from a later-described light source unit 24 and applies illuminating light to a living body, and an actuator 15 provided on the distal end side of the illumination fiber 14, the actuator 15 scanning a distal end of the illumination fiber 14 in a desired direction based on a drive signal from a later-described driver unit 25 are provided. Such configuration allows application of illuminating light from the light source unit 24, which is guided by the illumination fiber 14, to an object.

Also, inside the insertion portion 11, a detection fiber 16 inserted from the proximal end side to the distal end side along an inner periphery of the insertion portion 11, which serves as a light receiving section that receives return light from a subject, is provided. A distal end face of the detection fiber 16 is arranged in the periphery of the distal end optical system 13 at the distal end face of the distal end portion 12. The detection fiber 16 may include at least two fiber bundles. When the endoscope 2 is connected to the main body apparatus 3, the detection fiber 16 is connected to a later-described demultiplexer 36.

Furthermore, inside the insertion portion 11, a memory 17 that stores various types of information relating to the endoscope 2 is provided. When the endoscope 2 is connected to the main body apparatus 3, the memory 17 is connected to a later-described controller 23 via a non-illustrated signal wire and various types of information relating to the endoscope 2 are read by the controller 23.

The main body apparatus 3 includes a power supply 21, a memory 22, the controller 23, the light source unit 24, the driver unit 25 and a detection unit 26. The light source unit 24 includes three light sources 31*a*, 31*b* and 31*c* and a multiplexer 32.

The driver unit 25 includes a signal generator 33, digital/analog (hereinafter referred to as "D/A") converters 34*a* and 34*b*, and an amplifier 35.

The detection unit 26 includes the demultiplexer 36, detectors 37*a* to 37*c*, and analog/digital (hereinafter referred to as "A/D") converters 38*a* to 38*c*. The power supply 21 controls supply of power to the controller 23 in response to an operation of, e.g., a non-illustrated power supply switch. In the memory 22, e.g., a control program for performing overall control of the main body apparatus 3 is stored.

Upon supply of power from the power supply 21, the controller 23 reads the control program from the memory 22 and performs control of the light source unit 24 and the driver unit 25, and performs control to analyze a light intensity of return light from an object, which has been detected by the detection unit 26, and displays an acquired object image on the monitor 4.

The light sources 31*a*, 31*b* and 31*c* in the light source unit 24 emit light with respective wavelength bands that are different from one another, for example, light of R (red), G (green) and B (blue), to the multiplexer 32, under the control of the controller 23. The multiplexer 32 multiplexes the light with the wavelength bands of R, G and B, which has been emitted from the light sources 31*a*, 31*b* and 31*c*, and outputs the resulting light to the illumination fiber 14.

The signal generator 33 in the driver unit 25 outputs a drive signal for scanning the distal end of the illumination fiber 14 in a desired direction, for example, in a helical manner, under the control of the controller 23. More specifically, the signal generator 33 outputs a drive signal for driving the distal end of the illumination fiber 14 in a horizontal direction (X-axis direction) relative to an insertion axis of the insertion portion 11 to the D/A converter 34*a*, and outputs a drive signal for driving the distal end of the illumination fiber 14 in a vertical direction (Y-axis direction) relative to the insertion axis of the insertion portion 11 to the D/A converter 34*b*.

The D/A converters 34*a* and 34*b* perform conversion of the respective inputted drive signals from digital signals to analog signals and outputs the respective resulting drive signals to the amplifier 35. The amplifier 35 amplifies the inputted drive signals and outputs the resulting drive signals to the actuator 15. The actuator 15, which serves as a drive section, swings the distal end (free end) of the illumination fiber 14 based on the drive signals from the amplifier 35 to helically scan the distal end. Consequently, light emitted from the light source unit 24 to the illumination fiber 14 is sequentially applied to a subject in a helical manner.

The detection fiber 16 receives return light resulting from reflection by a surface region of the subject and guides the received return light to the demultiplexer 36. The demultiplexer 36, which is, for example, a dichroic mirror or the like, demultiplexes the return light into predetermined wavelength bands. More specifically, the demultiplexer 36 demultiplexes the return light guided by the detection fiber 16 into return light with wavelength bands of R, G and B and outputs the return light to the detectors 37*a*, 37*b* and 37*c*, respectively.

The detectors 37*a*, 37*b* and 37*c* detect respective light intensities of the return light with the wavelength bands of R, G and B. The signals of the light intensities detected by the detectors 37*a*, 37*b* and 37*c* are outputted to the A/D converters 38*a*, 38*b* and 38*c*, respectively. The A/D converters 38*a* to 38*c* perform conversion of the respective signals of the light intensities outputted from the detectors 37*a* to 37*c* from analog signals to digital signals, and output the resulting signals to the controller 23.

The controller 23 performs predetermined image processing on the digital signals from the A/D converters 38*a* to 38*c* to generate an object image and displays the object image on the monitor 4.

Here, a detailed configuration of the actuator 15 provided inside the insertion portion 11 will be described with reference to FIG. 2.

As illustrated in FIG. 2, a ferrule 41, which serves as a joining member, is arranged between the illumination fiber 14 and the actuator 15. The ferrule 41 is a member used in the field of optical communications, and for a material thereof, i.e., zirconia (ceramic) or nickel is used, enabling processing to form a center hole with high precision (for example, ±1 μm) relative to an outer diameter (for example, 125 μm) of the illumination fiber 14 to be performed easily.

As illustrated in FIG. 2, the ferrule 41 has a quadrangular prism shape and includes side faces 42*a* and 42*c* perpendicular to the X-axis direction and side faces 42*b* and 42*d* perpendicular to the Y-axis direction. Note that the shape of the ferrule 41 is not limited to a quadrangular prism shape, and only needs to be a prism shape. At a substantial center of the ferrule 41, processing to form a center hole is performed based on the diameter of the illumination fiber 14, and the illumination fiber 14 is fixed in the center hole via, e.g., an adhesive. The processing to form a center hole is performed so as to provide a smallest possible clearance (gap) and a thinnest possible adhesive layer. Also, for the adhesive, a low-viscosity one is used.

The actuator 15 includes actuators 15*a* to 15*d*, and the actuators 15*a* to 15*d* are positioned on the respective side faces 42*a* to 42*d* of the quadrangular prism-shaped ferrule 41, respectively. Each of the actuators 15*a* to 15*d* is, for example, a piezo element and expands/contracts in response to a drive signal from the driver unit 25. In particular, each of the actuators 15*a* and 15*c* is driven in response to a drive signal from the D/A converter 34*a*, and each of the actuators 15*b* and 15*d* are driven in response to a drive signal from the D/A converter 34*b*. Consequently, the actuators 15*a* to 15*d* cause the distal end of the illumination fiber 14 to swing to helically scan the distal end of the illumination fiber 14. Note that each of the actuators 15*a* to 15*d* is not limited to a piezo element and may be, for example, an electromagnetically-driven coil.

If a conductive material such as nickel is used for the ferrule 41, the ferrule 41 itself is made to serve as a GND electrode of each of the actuators 15*a* to 15*d*. Also, if a non-conductive material such as zirconia is used for the ferrule 41, processing to form a conductive layer on a surface of the ferrule 41 is performed to provide a GND electrode of each of the actuators 15*a* to 15*d*.

As described above, insertion of the ferrule 41, which is a joining member subjected to high-precision processing to form a center hole, between the actuator 15 and the illumination fiber 14 allows the endoscope 2 to include a thinnest possible adhesive layer required for fixation between the illumination fiber 14 and the ferrule 41, achieve largest possible reduction of an impact of temperature change and perform stable driving of the illumination fiber 14.

Figure 3:
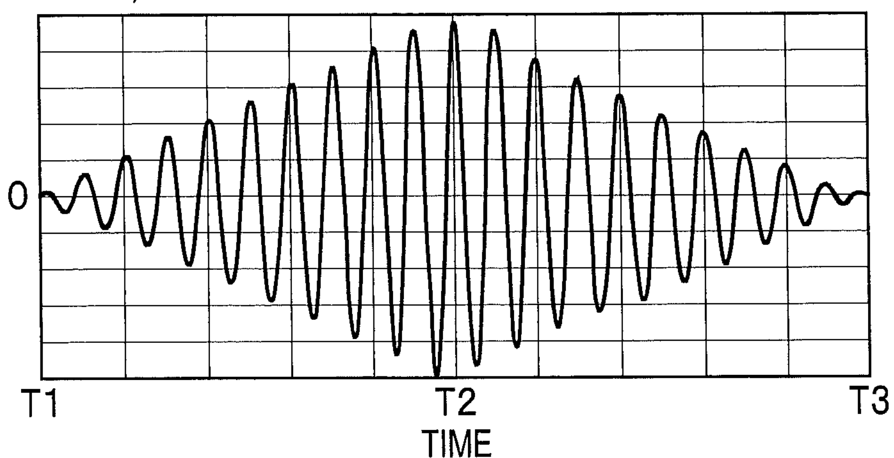
FIG. 3 includes diagrams illustrating a configuration of an endoscope apparatus including a scanning endoscope: diagrams for describing an example of waveforms of signals supplied to an actuator.
Figure 3:
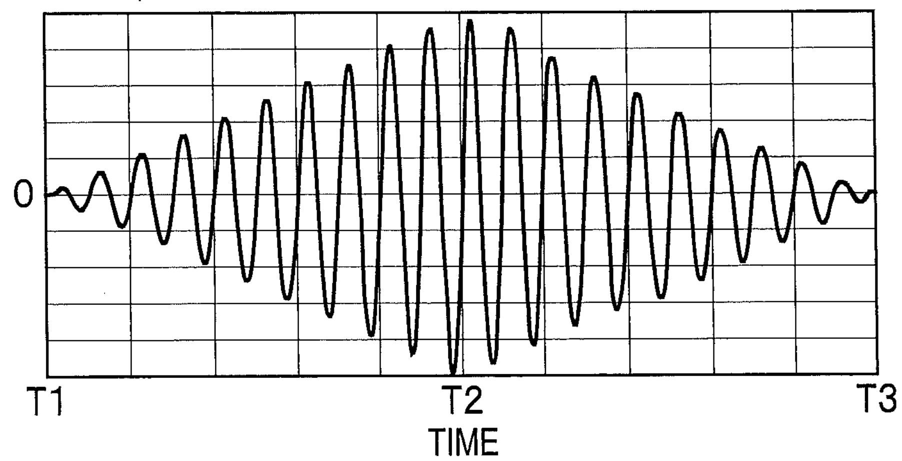
Figure 4:
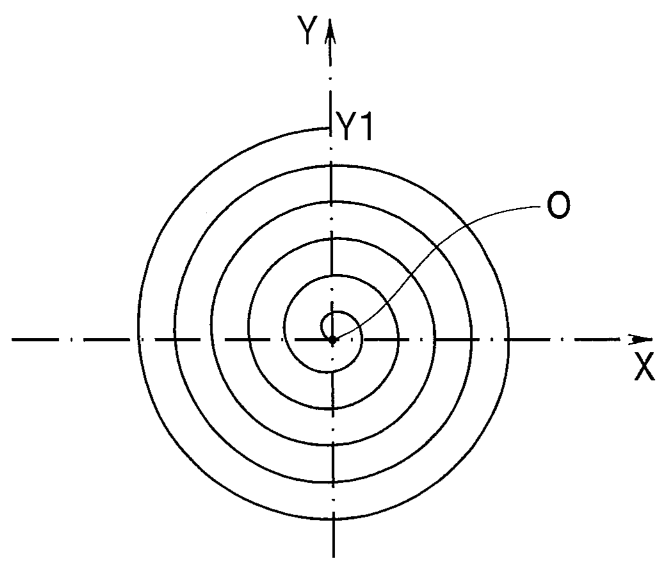
FIG. 4 is a diagram illustrating a configuration of an endoscope apparatus including a scanning endoscope: a diagram for describing an example of a locus of a scan of an illumination fiber.

Next, an operation of the endoscope apparatus 1 configured as described above will be described below with reference to FIGS. 3 and 4. FIG. 3 includes diagrams for describing an example of waveforms of signals supplied to the actuator 15, and FIG. 4 is a diagram for describing an example of a locus of a scan of the illumination fiber 14.

Note that FIG. 3(*a*) indicates a signal waveform of a drive signal outputted from the D/A converter 34*a* via the amplifier 35. The signal waveform is of a drive signal for driving the illumination fiber 14 in the X-axis direction and supplied to the actuators 15*a* and 15*c*.

FIG. 3(*b*) indicates a signal waveform of a drive signal outputted from the D/A converter 34*b* via the amplifier 35. The signal waveform is of a drive signal for driving the illumination fiber 14 in the Y-axis direction and supplied to the actuators 15*b* and 15*d*.

The signal waveform for the Y-axis direction is a signal waveform that is 90° out of phase relative to the signal waveform for the X-axis direction. More specifically, the difference in phase between the signal waveform for the X-axis direction and the signal waveform for the Y-axis direction can be calculated according to (Expression 1) below if a vibration axis count N is an even number, and according to (Expression 2) below if the vibration axis count N is an odd number.

$$\text{Phase difference} = 360°/(2 \times \text{vibration axis count } N) \qquad \text{(Expression 1)}$$

$$\text{Phase difference} = 360°/\text{vibration axis count } N \qquad \text{(Expression 2)}$$

In the present embodiment, the vibration axis count N is 2 (even number: the X-axis and the Y-axis), and thus, the phase difference is 90° according to (Expression 1) above.

As described above, the driver unit 25 provides a control section that generates a first drive signal to be outputted to the actuators 15*a* and 15*c*, and a second drive signal to be outputted to the actuators 15*b* and 15*d*, and controls a difference in phase between the first drive signal and the second drive signal based on a vibration axis count N.

As illustrated in FIGS. 3(*a*) and 3(*b*), an amplitude of each of the signal waveforms gradually increases from a time T1 to a time T2 and have a largest amplitude value at the time T2. Then, the amplitude of the signal waveform gradually decreases from the time T2 to a time T3, and has a smallest amplitude value at the time T3.

A locus of a scan of the illumination fiber 14 in this case is the locus indicated in FIG. 4. The distal end of the illumination fiber 14 is positioned at an intersection O between the X-axis and the Y-axis at the time T1. Then, as the amplitudes of the signal waveforms increase from the time T1 to the time T2, the distal end of the illumination fiber 14 is helically scanned outward from the intersection O, and at the time T2, is positioned at, for example, a position of an intersection Y1 with the Y-axis. Furthermore, as the amplitudes of the signal waveforms decrease from the time T2 to the time T3, the distal end of the illumination fiber 14 is helically scanned inward from the intersection Y1 and positioned at the intersection O at the time T3 although not illustrated.

As described above, in the endoscope 2, the ferrule 41, which is a joining member subjected to processing with precision to form a center hole, is inserted between the actuator 15 and the illumination fiber 14. Consequently, reduction in thickness of the adhesive layer required for fixation between the illumination fiber 14 and the ferrule 41 and largest possible reduction of an impact of temperature change are achieved. Accordingly, the endoscope has a configuration that is less affected by temperature change and enables the illumination fiber to be stably driven without feedback control.

(First Embodiment)

Next, a calibration tool for a scanning endoscope according to a first embodiment of the present invention, which is provided for calibration of a locus of a scan of light in the scanning endoscope 2 as described above, will be described with reference to the drawings.

Figure 5:
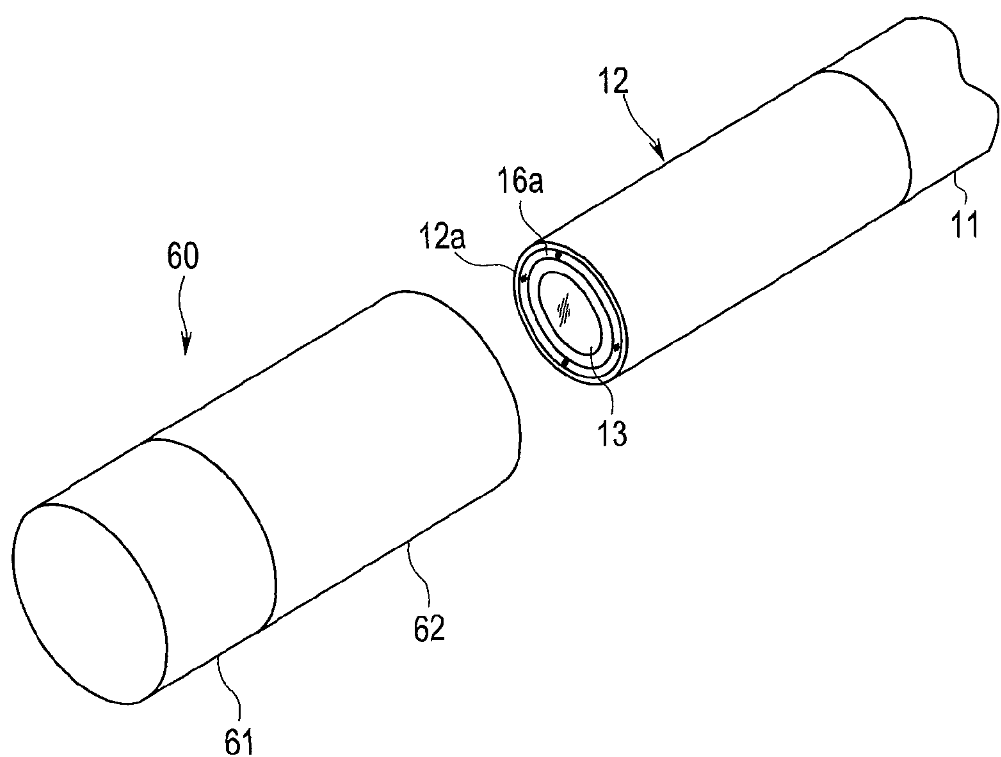
FIG. 5 relates to a first embodiment of the present invention, and is a perspective diagram illustrating a configuration of a calibration tool for a scanning endoscope into which an insertion portion is to be inserted.
Figure 6:
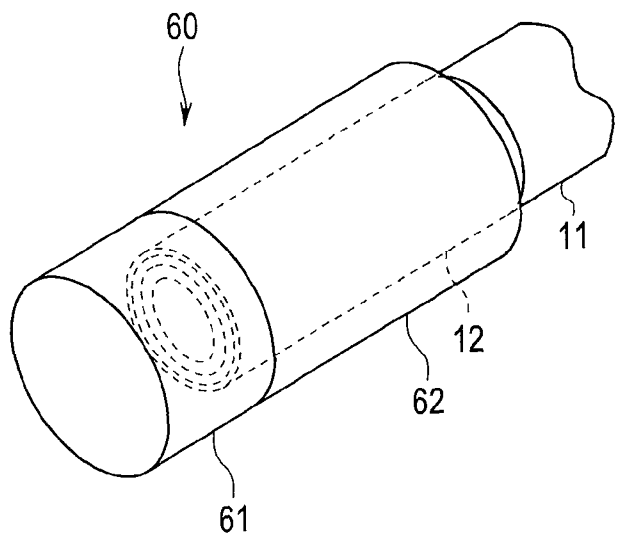
FIG. 6 relates to the first embodiment of the present invention, and is a perspective diagram illustrating a calibration tool for a scanning endoscope with an insertion portion inserted therein.
Figure 7:
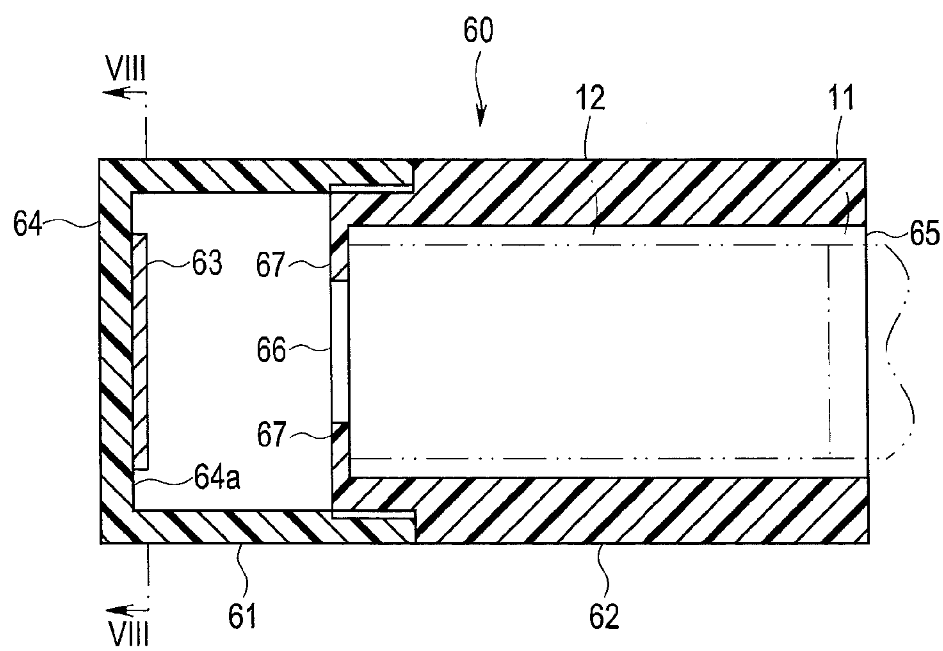
FIG. 7 relates to the first embodiment of the present invention, and is a cross-sectional diagram illustrating a configuration of a calibration tool for a scanning endoscope.
Figure 8:
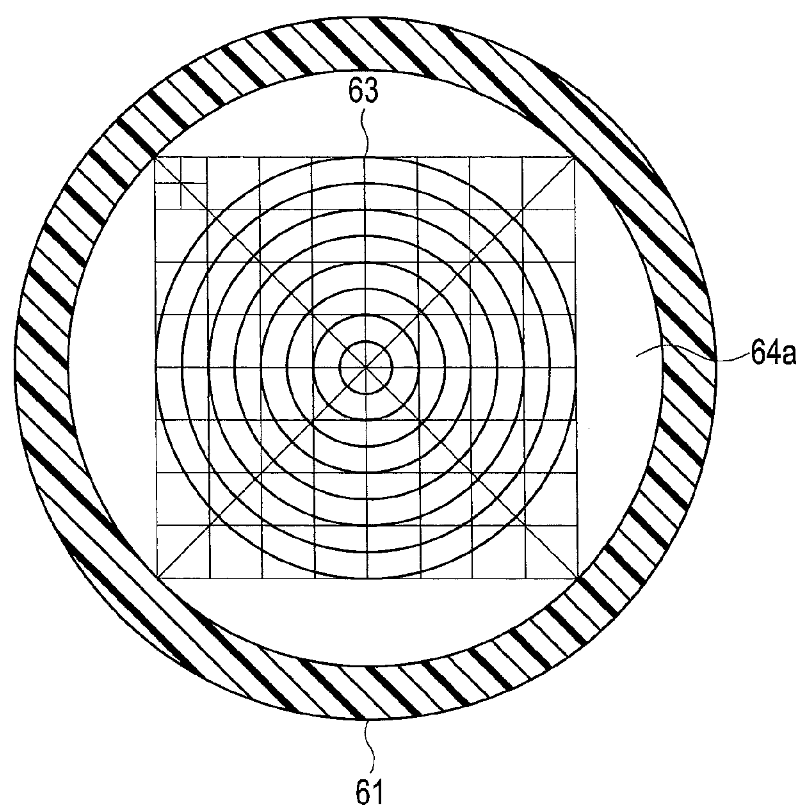
FIG. 8 relates to the first embodiment of the present invention, and is a cross-sectional view along line VIII-VIII in FIG. 7.
Figure 9:
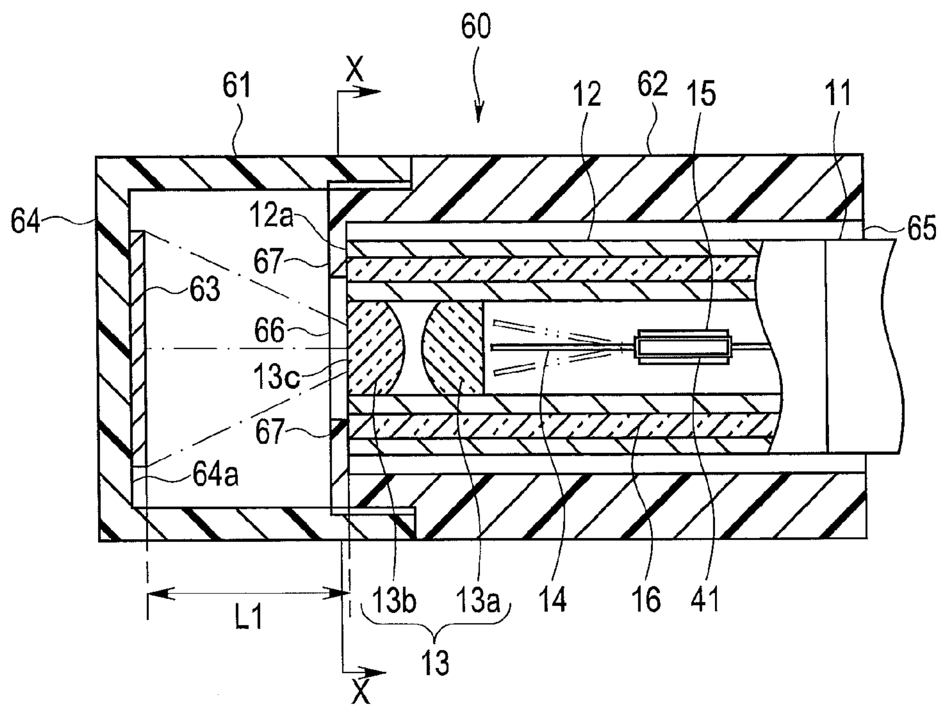
FIG. 9 relates to the first embodiment of the present invention, and is a cross-sectional diagram illustrating a calibration tool for a scanning endoscope with an insertion portion inserted therein.
Figure 10:
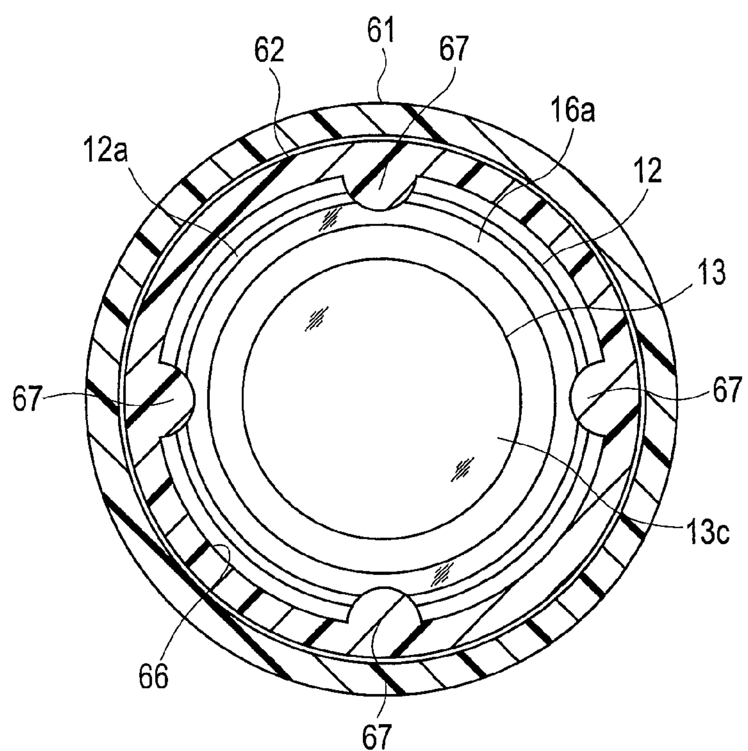
FIG. 10 relates to the first embodiment of the present invention, and is a cross-sectional view along line X-X in FIG. 9.
Figure 11:
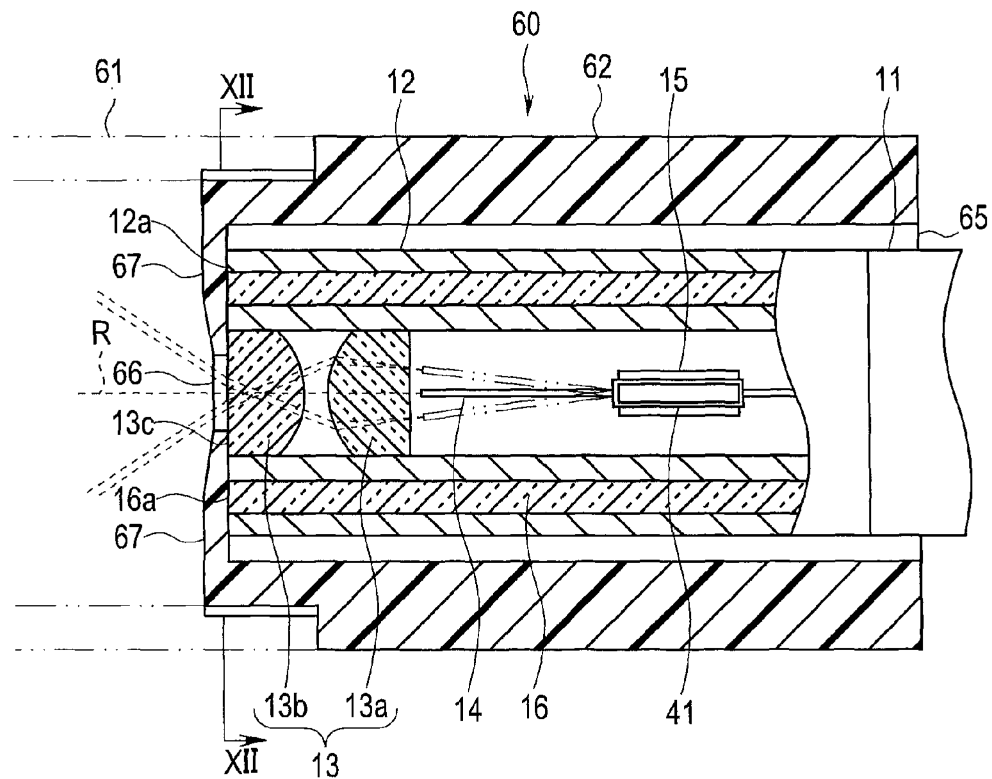
FIG. 11 relates to the first embodiment of the present invention, and is a cross-sectional diagram illustrating a configuration of a calibration tool for a scanning endoscope according to a modification, with an insertion portion inserted therein.
Figure 12:
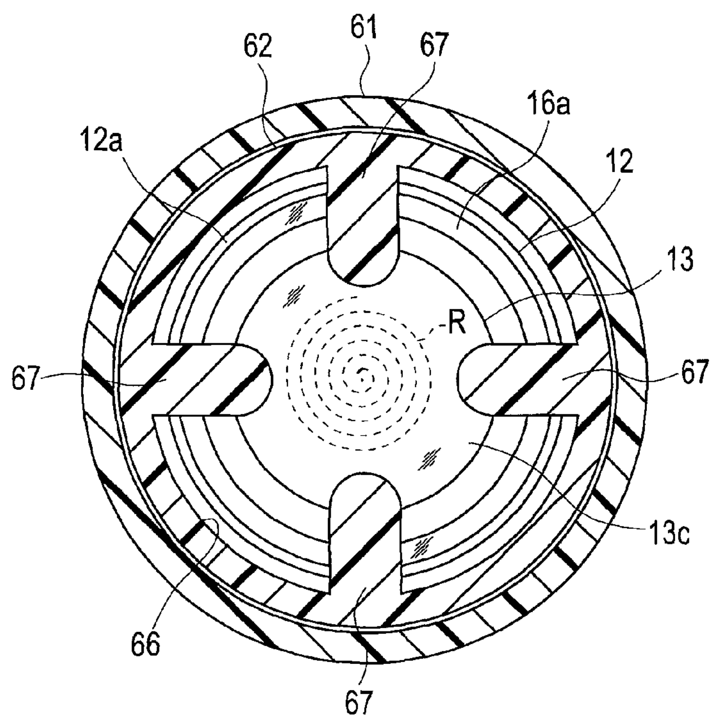
FIG. 12 relates to the first embodiment of the present invention, and is a cross-sectional view along line XII-XII in FIG. 11.
Figure 13:
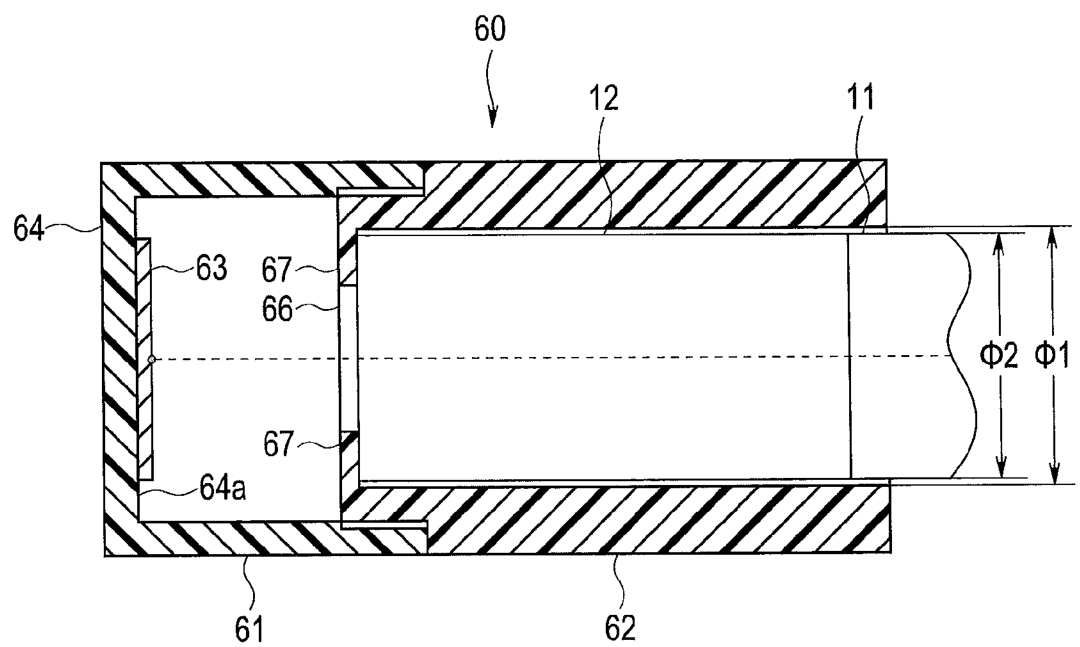
FIG. 13 relates to the first embodiment of the present invention, and is a cross-sectional diagram illustrating an example of a configuration for axis alignment of an insertion portion inserted in a calibration tool for a scanning endoscope.

FIGS. 5 to 13 relate to a first embodiment of the present invention: FIG. 5 is a perspective diagram illustrating a configuration of a calibration tool for a scanning endoscope into which an insertion portion is to be inserted; FIG. 6 is a perspective diagram illustrating a calibration tool for a scanning endoscope with an insertion portion inserted therein; FIG. 7 is a cross-sectional diagram illustrating a configuration of a calibration tool for a scanning endoscope; FIG. 8 is a cross-sectional view along line VIII-VIII in FIG. 7; FIG. 9 is a cross-sectional diagram illustrating a calibration tool for a scanning endoscope with an insertion portion inserted therein; FIG. 10 is a cross-sectional view along line X-X in FIG. 9; FIG. 11 is a cross-sectional diagram illustrating a configuration of a calibration tool for a scanning endoscope according to a modification, with an insertion portion inserted therein; FIG. 12 is a cross-sectional view along line XII-XII in FIG. 11; and FIG. 13 is a cross-sectional diagram illustrating a configuration for axis alignment of an insertion portion inserted in a calibration tool for a scanning endoscope.

As illustrated in FIGS. 5 to 7, a calibration tool for a scanning endoscope (hereinafter simply referred to as "calibration tool") 60 according to the present embodiment is a bottomed cylindrical body with one end occluded. The calibration tool 60 includes a bottomed cylindrical portion 61 disposed on the distal end side and a bottomless cylindrical portion 62 disposed on the proximal end side, the bottomless cylindrical portion 62 being, here, threadably connected to the bottomed cylindrical portion 61 so as to be continuous with the bottomed cylindrical portion 61 (see FIG. 7). Note that connection and fixation between the bottomed cylindrical portion 61 and the bottomless cylindrical portion 62 is not limited to thread connection, and, e.g., fitting, press fitting or screw fastening may be employed. The distal end side of the insertion portion 11 of the above-described endoscope 2 is inserted to the calibration tool 60 from an opening portion 65 on the proximal side of the bottomless cylindrical portion 62, and the calibration tool 60 has a length allowing the distal end portion 12 to be substantially accommodated.

On the distal end side of the bottomed cylindrical portion 61, a bottom portion 64 that occludes an end portion is provided. On a wall surface (bottom face) 64*a* on the inner side of the bottom portion 64, a panel-like chart 63 with a calibration pattern drawn on a surface thereof by, e.g., printing, the calibration pattern being a pattern that is point-symmetrical with respect to a center, is provided as illustrated in FIG. 8. The calibration pattern drawn on the chart 63 has a size set according to a focal length set for the endoscope 2. Note that it is desirable that the bottomed cylindrical portion 61 includes a black resin or an inner wall surface thereof is painted in black.

As illustrated in FIGS. 9 and 10, in the bottomless cylindrical portion 62, a plurality of, here, four projection portions 67, which each serve as an abutment portion provided so as to extend inward in a radial direction from an opening portion 66 on the distal end side that is threadably connected to the bottomed cylindrical portion 61, are formed. In other words, these four projection portions 67 are formed so as to project inward from an opening end on the distal end side of the bottomless cylindrical portion 62. It is desirable that the bottomless cylindrical portion 62 also includes a black resin or a wall surface on the side of a space formed as a result of connecting the bottomless cylindrical portion 62 to the bottomed cylindrical portion 61, that is, a distal end face with the projection portions 67 formed therein, is painted in black.

For these four projection portions 67, a projection amount allowing the distal end face 12*a* of the distal end portion 12 of the inserted endoscope 2 to be in contact with and abut the four projection portions 67 is set. Here, the four projection portions 67 are formed so as to project inward to respective positions where the projection portions 67 cover predetermined areas of the detection window 16*a* for the detection fiber 16 provided in the distal end face 12*a* of the distal end portion 12 from the outside.

Also, in each of the four projection portions 67, the area that covers the detection window 16*a* has a size (area) enabling securement of an exposed area of the detection window 16*a* enough to detect return light via the detection fiber 16, or may be transparent (light transmissive). Note that it is desirable that the four projection portions 67 do not cover the detection window 16*a* of the detection fiber 16 and are in contact with only respective portions of the barrel on the outer side of the detection window 16*a* of the distal end face 12*a*.

The detection window 16*a* of the endoscope 2 is one with a thin film of transparent resin formed on the end face of the detection fiber 16, and planarly formed to be in plane with the distal end face 12*a* of the distal end portion 12 so that a position of a surface of the detection window 16*a* coincides with a position of the distal end face 12*a*. Note that the detection window 16*a* is not limited to one including a transparent resin and may be, e.g., one including a transparent cover glass.

Furthermore, although the four projection portions 67 each have a semi-circular shape as illustrated in FIG. 10, the shape of the four projection portions 67 is not limited to such shape. Also, an illumination window 13*c* (see FIGS. 9 and 10) for the distal end optical system 13 including the illumination lenses 13*a* and 13*b* in the endoscope 2 is planarly formed in plane with the distal end face 12*a* of the distal end portion 12 so that a position of a surface of the illumination window 13*c* coincides with the position of the distal end face 12*a*.

Note that although the four projection portions 67 are configured so as to abut the surface of the detection window 16*a* in the above description, it is desirable that each of the four projection portions 67 is in contact with and abuts a part of the distal end face 12*a* of the distal end portion 12, the part projecting furthest toward the distal end side.

The calibration tool 60 according to the present embodiment, which is configured as described above allows a distal end part of the insertion portion 11 of the endoscope 2 to be inserted thereto from the opening portion 65 at a proximal end of the bottomless cylindrical portion 62, and the distal end face 12*a* of the distal end portion 12 is brought into contact with the four projection portions 67, whereby the amount of the insertion is determined In such state, a predetermined distance L1 (see FIG. 9) between the distal end face 12*a* of the distal end portion 12 of the endoscope 2 and the surface of the chart 63 provided on the wall surface of the bottomed cylindrical portion 61 in the calibration tool 60 is defined. Note that in the calibration tool 60, the bottom portion 64 and the four projection portions 67 are configured so that the distal end face 12*a* of the distal end portion 12 and the surface of the chart 63 provided on the wall surface of the bottomed cylindrical portion 61 face each other in parallel and the calibration pattern on the chart 63 and the distal end face 12*a* of the distal end portion 12 are arranged in parallel.

The predetermined distance L1 above is a proper distance for the endoscope 2 here to detect return light of illuminating light to perform image calibration in image processing, and is set to an ideal distance from the distal end face 12*a* of the distal end portion 12 to the surface of the chart 63 according to the size of the calibration pattern on the chart 63. In other words, for the predetermined distance L1, an ideal calibration distance to the surface of the chart 63 for calibrating an image acquired by the endoscope 2, which is a distance obtained by subtracting a thickness of the chart 63 provided on the wall surface 64*a*, which is the bottom face of the bottomed cylindrical portion 61, from a length in an axial direction (longitudinal axis) of the space in the bottomed cylindrical portion 61 formed as a result of the bottomless cylindrical portion 62 being joined to the bottomed cylindrical portion 61 and adding a thickness of the projection portions 67 formed at the distal end of the bottomless cylindrical portion 62 to the length, is defined. Note that the bottomed cylindrical portion 61 has a length in the axial direction (longitudinal axis) set according to the predetermined distance L1. Also, the calibration pattern (see FIG. 8) may be one directly drawn on the wall surface 64*a* of the bottomed cylindrical portion 61.

When the endoscope 2 calibrates an acquired image, a distance from a position of a surface of the illumination window 13*c* of the distal end optical system 13, from which illuminating light exits, to the calibration pattern on the chart 63 is important. Therefore, as illustrated in FIGS. 11 and 12, the four projection portions 67 may have an amount of projection allowing the four projection portions 67 to be in contact with and abut the surface of the illumination window 13*c* of the distal end optical system 13. Note that the amount of projection of each of the four projection portions 67 is set so that the projection portion 67 remains within a surface region of the illumination window 13*c* in which a light beam R of illuminating light applied from the illumination fiber 14 and refracted by the distal end optical system 13 does not pass through. In other words, the four projection portions 67 are in contact with the surface of the illumination window 13*c* at respective positions where the projection portions 67 do not interrupt illuminating light.

As described above, in the endoscope 2, the four projection portions 67 are brought into contact with the surface of the illumination window 13*c* of the distal end portion 12, and an insertion position in an insertion direction, that is, a longitudinal axis direction, of the insertion portion 11 inserted in the calibration tool 60 is determined and thus defined, enabling image calibration to be performed with a proper and ideal predetermined distance L1.

Furthermore, as described above, the endoscope 2 has a configuration in which the center of the distal end optical system 13 is provided so as to coincide with the center of the distal end face 12*a* of the distal end portion 12, and thus, in order to define center positions of the calibration tool 60 and the distal end portion 12 of the insertion portion 11, for example, as illustrated in FIG. 13, a hole diameter $\phi 2$ of the bottomless cylindrical portion 62 may be set so as to coincide with an outer diameter $\phi 1$ of the distal end portion 12 of the insertion portion 11, for example, within an error range of 0.01 mm ($\phi 1 = \phi 2 \pm 0.01$ mm), enabling alignment of the centers in a radial direction of the calibration tool 60 and the distal end portion 12 with mechanical precision.

Consequently, a spot of illuminating light exiting from the illumination fiber 14 when the illumination fiber 14 in the endoscope 2 is not scanned coincides with the center of the calibration pattern, enabling a proper and ideal center position of the distal end portion 12 of the endoscope 2 relative to the calibration pattern to be defined. Note that a center of a scan of illuminating light applied from the illumination fiber 14 when the illumination fiber 14 in the endoscope 2 is scanned coincides with the center of the calibration pattern by making the position of the spot of the illuminating light applied when the illumination fiber 14 in the endoscope 2 is not scanned coincide with the center of the calibration pattern.

As described above, the calibration tool 60 according to the present embodiment can have a configuration that enables easy positioning of the distal end portion 12 of the endoscope 2 to an attachment position where image calibration can correctly be performed.

(Second Embodiment)

Next, a calibration tool for a scanning endoscope according to a second embodiment of the present invention will be described.

Figure 14:
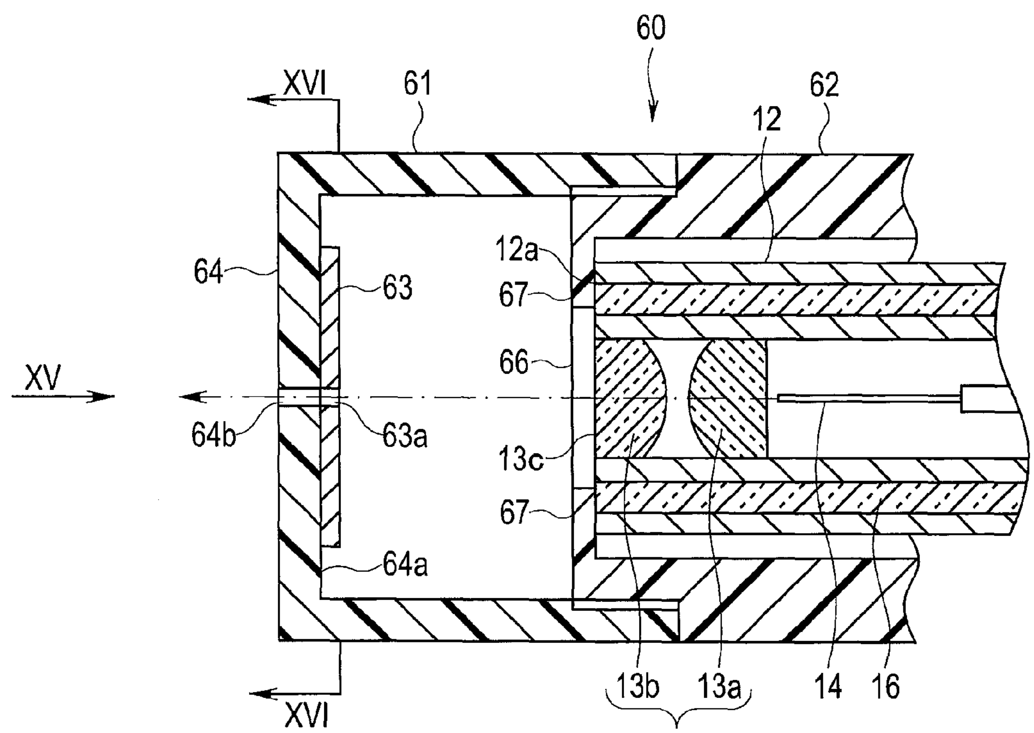
FIG. 14 relates to a second embodiment of the present invention, and is a cross-sectional diagram illustrating a configuration of a calibration tool for a scanning endoscope with an insertion portion inserted therein.
Figure 15:
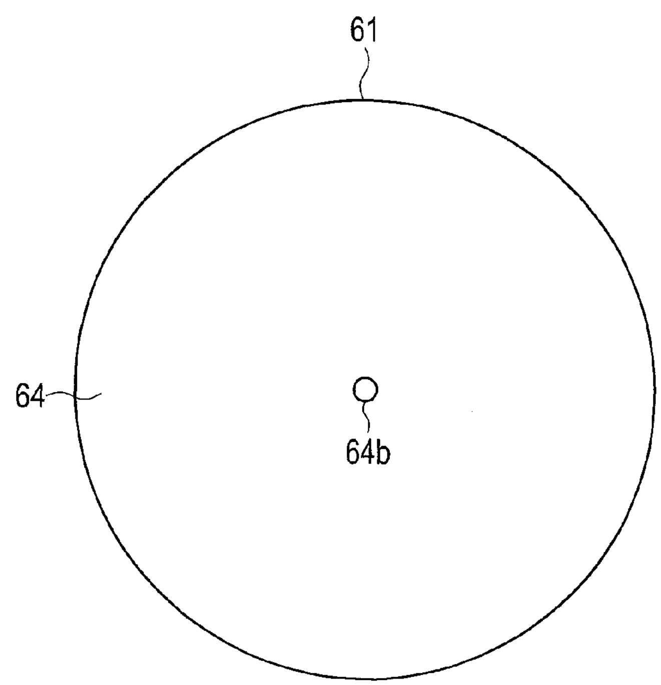
FIG. 15 relates to the second embodiment of the present invention, and is a view in the direction of arrow XV in FIG. 14.
Figure 16:
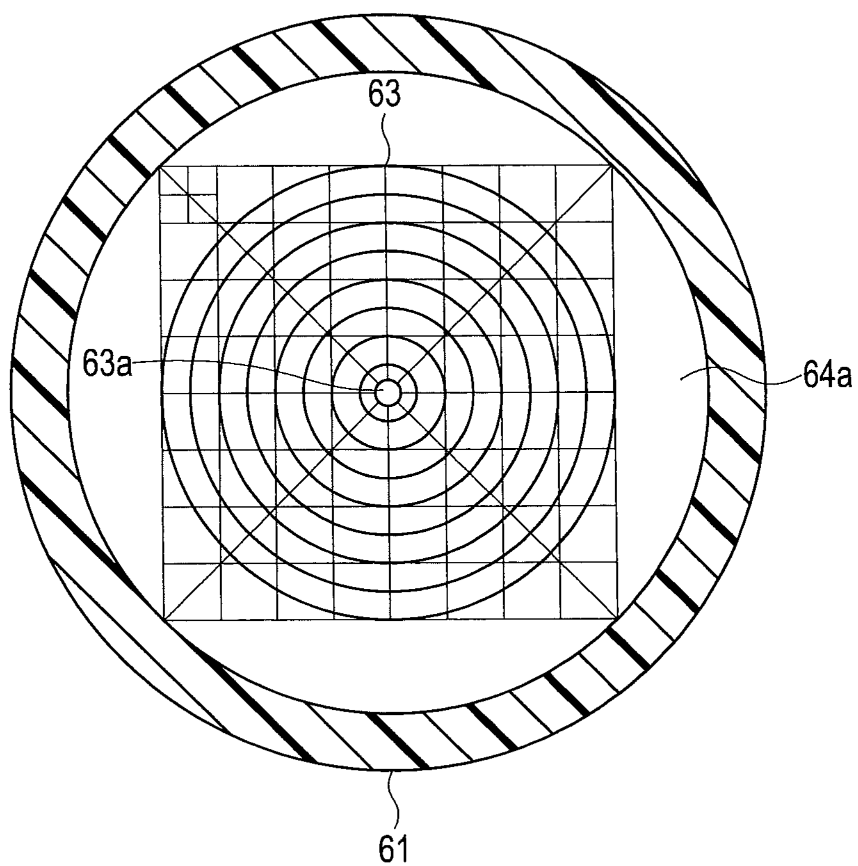
FIG. 16 relates to a second embodiment of the present invention, and is a cross-sectional view along line XVI-XVI in FIG. 14.
Figure 17:
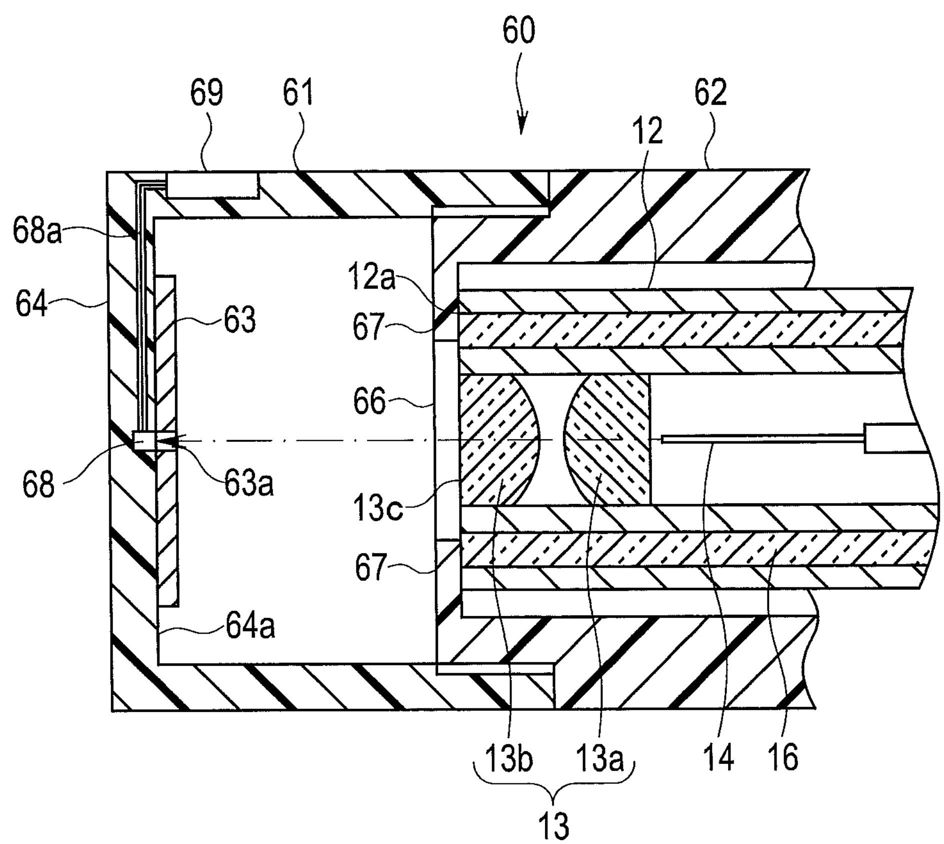
FIG. 17 relates to a second embodiment of the present invention, and is a cross-sectional diagram illustrating a configuration of a calibration tool for a scanning endoscope according to a modification, with an insertion portion inserted therein.

FIGS. 14 to 17 relates to a second embodiment of the present invention: FIG. 14 is a cross-sectional diagram illustrating a configuration of a calibration tool for a scanning endoscope with an insertion portion inserted therein; FIG. 15 is a view in the direction of arrow XV in FIG. 14; FIG. 16 is a cross-sectional view along line XVI-XVI in FIG. 14; and FIG. 17 is a cross-sectional diagram illustrating a configuration of a calibration tool for a scanning endoscope according to a modification, with an insertion portion inserted therein. A configuration of a calibration tool 60 for a scanning endoscope here is a modification of the first embodiment, and components that have been described are provided with reference numerals that are the same as those of the first embodiment and a description thereof will be omitted.

Here, as described above, a configuration that enables easy center alignment of a distal end portion 12 with a calibration tool 60 in a radial direction in the calibration tool 60 used for calibration of an image acquired by an endoscope 2, in which a center of a distal end optical system 13 is provided so as to coincide with a distal end face 12*a* of the distal end portion 12, will be indicated as an example.

More specifically, as illustrated in FIGS. 14 and 15, the calibration tool 60 according to the present embodiment includes a through hole 64*b* formed at a center of a bottom portion 64 of a bottomed cylindrical portion 61, the through hole 64*b* having a size substantially equal to a size of a spot of illuminating light from a illumination fiber 14. As illustrated in FIGS. 14 and 16, a chart 63 also includes a through hole 63*a* formed at a center of a calibration pattern drawn on a surface thereof, the through hole 63*a* having a size that is substantially equal to the size of the through hole 64*b* of the bottom portion 64. Also, in the calibration tool 60, the chart 63 is disposed on the bottom portion 64 of the bottomed cylindrical portion 61 in such a manner that the respective through holes 64*b* and 63*a* overlap and communicate with each other.

When calibration of an image acquired by the endoscope 2 using the calibration tool 60 configured as described above, a user aligns a position in the radial direction of the distal end portion 12 of the endoscope 2 inserted in a bottomless cylindrical portion 62 with a position where illuminating light applied from the illumination fiber 14 that is not scanned passes through the respective through holes 64*b* and 63*a* formed at the respective centers of the bottom portion 64 and the chart 63 in the bottomed cylindrical portion 61 in communication with each other, enabling easy center alignment in the radial direction between the calibration tool 60 and the distal end portion 12. In other words, the user can make center alignment in the radial direction between the calibration tool 60 and the distal end portion 12 merely by adjusting the position in the radial direction of the distal end portion 12 to a position where illuminating light from the endoscope 2 can be viewed from the through hole 64*b* in the bottom portion 64. Here also, it should be understood that a center of a scan of illuminating light applied from the illumination fiber 14 when the illumination fiber 14 in the endoscope 2 is scanned coincides with the center of the calibration pattern by aligning the position of the spot of the illuminating light applied when the illumination fiber 14 is not scanned with the respective through holes 64*b* and 63*a* formed at the respective centers of the bottom portion 64 and the chart 63 in the bottomed cylindrical portion 61 so that the illuminating light passes through the respective through holes 64*b* and 63*a*.

Note that, as illustrated in FIG. 17, the calibration tool 60 may have a configuration in which a photodetector 68 overlapping the through hole 63*a* of the chart 63 is provided at the center of the bottom portion 64 of the bottomed cylindrical portion 61 and an indicator apparatus 69 connected to the photodetector 68 via a wiring 68*a*, the indicator apparatus 69 including, e.g., an LED to be turned on/off, is provided in an outer peripheral portion of the bottomed cylindrical portion 61. Note that each of the photodetector 68 and the indicator apparatus 69 is supplied with power via a power supply cord provided in the calibration tool 60, the power supply cord being connected to a battery or an external power supply (both of the power supply cords not illustrated).

In the calibration tool 60 configured as described above, when illuminating light applied from the illumination fiber 14 that is not scanned passes through the through hole 63*a* of the chart 63 and is detected by the photodetector 68, the indicator apparatus 69 is, e.g., turned on. Consequently, the user can easily make center position alignment in the radial direction between the calibration tool 60 and the distal end portion 12 by adjusting the position in the radial direction of the distal end portion 12 of the endoscope 2 inserted in the bottomless cylindrical portion 62 of the calibration tool 60 to a position that causes the indicator apparatus 69 to, e.g., be turned on.

(Third Embodiment)

Next, a calibration tool for a scanning endoscope according to a third embodiment according to the present invention will be described. Note that, here, a configuration in which a position adjustment mechanism, which serves as a centering adjustment mechanism that adjusts a center position in a radial direction of a distal end portion 12 to that of a calibration tool 60 and fixes the position of the distal end portion 12 in addition to the configuration of the second embodiment described above will be indicated as an example.

Figure 18:
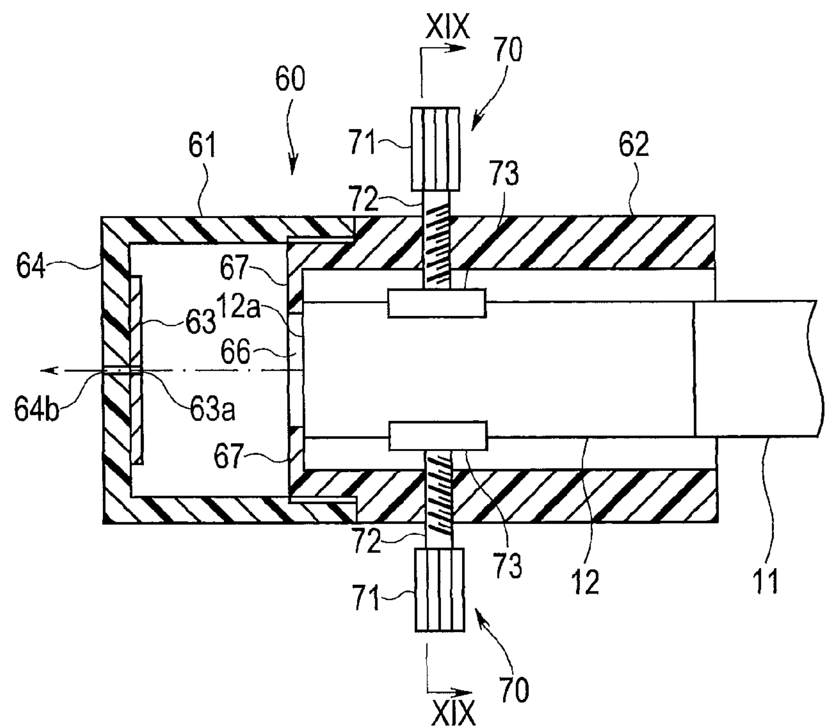
FIG. 18 relates to a third embodiment, and is a cross-sectional diagram illustrating a configuration of a calibration tool for a scanning endoscope with an insertion portion inserted therein, the calibration tool including a position adjustment mechanism.
Figure 19:
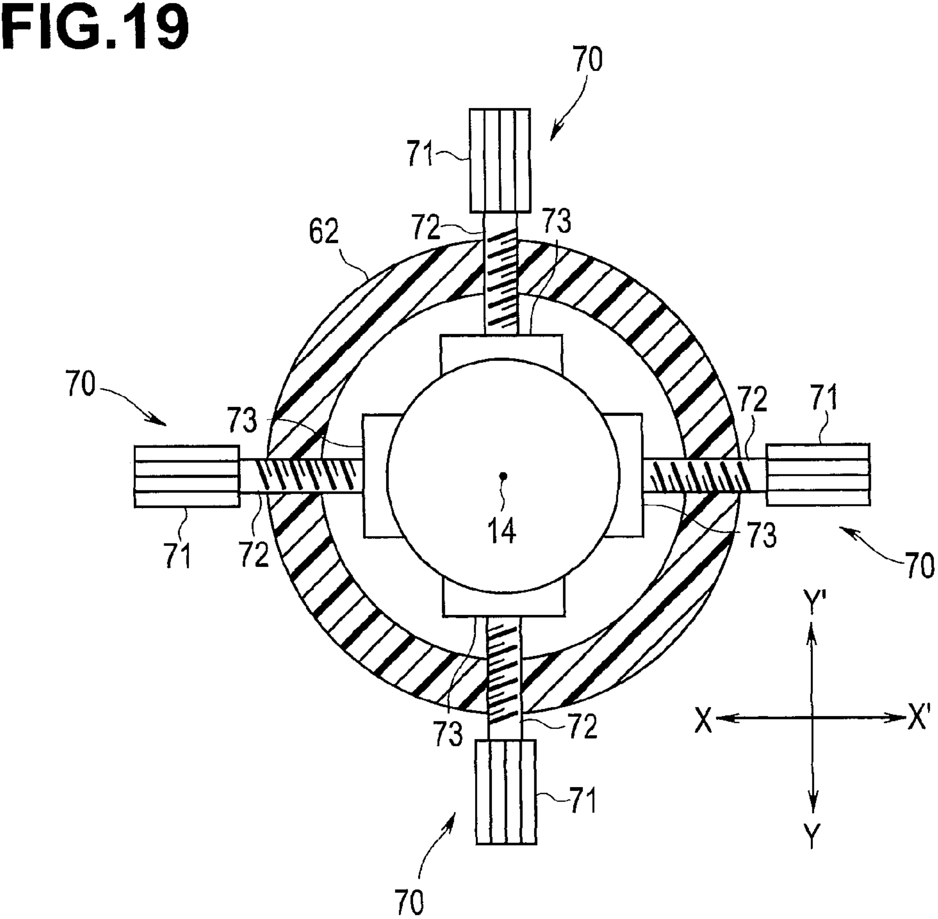
FIG. 19 relates to the third embodiment, and is a cross-sectional view along line XIX-XIX in FIG. 18.
Figure 20:
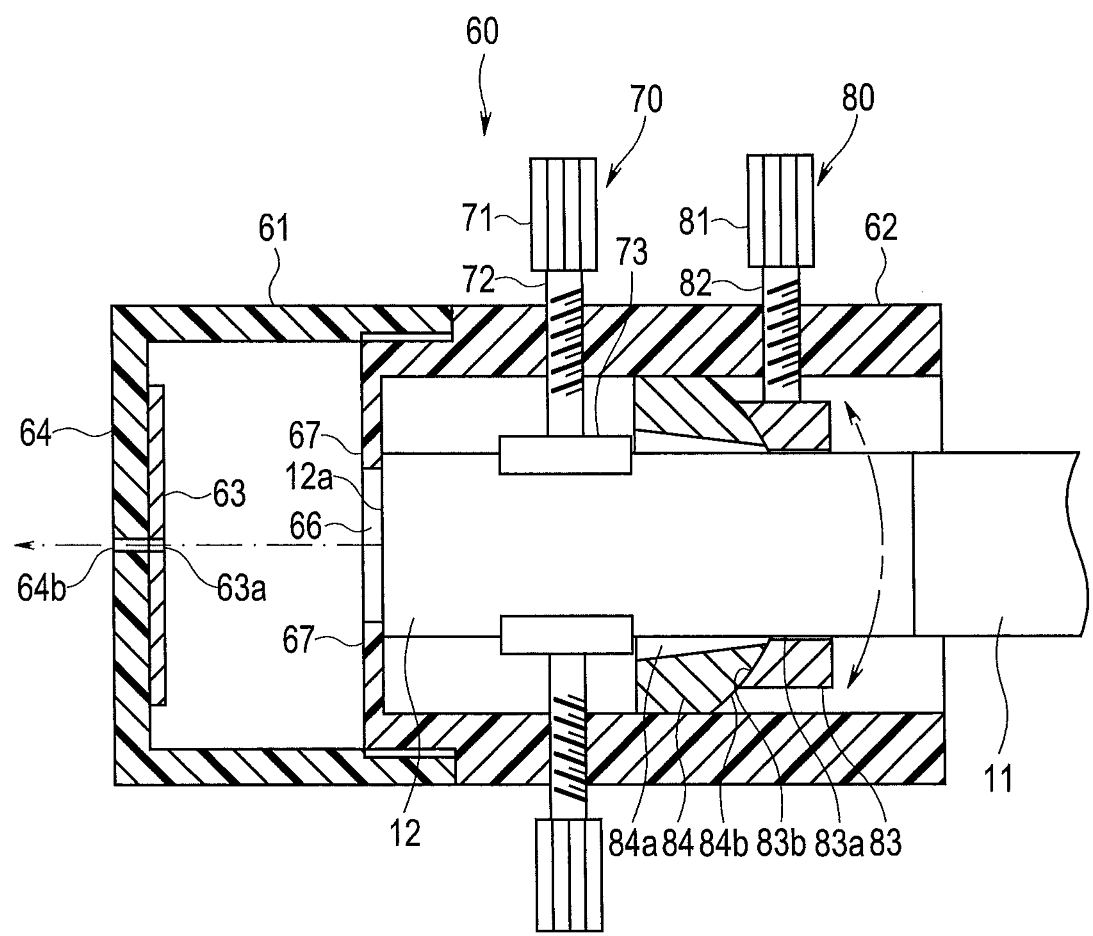
FIG. 20 relates to the third embodiment, and is a cross-sectional diagram illustrating a configuration of a calibration tool for a scanning endoscope with an insertion portion inserted therein, the calibration tool including an inclination adjustment mechanism in addition to a position adjustment mechanism.

FIGS. 18 to 20 relate to a third embodiment of the present invention: FIG. 18 is a cross-sectional diagram illustrating a configuration of a calibration tool for a scanning endoscope with an insertion portion inserted therein, the calibration tool including a position adjustment mechanism; FIG. 19 is a cross-sectional view along line XIX-XIX in FIG. 18; and FIG. 20 is a cross-sectional diagram illustrating a configuration of a calibration tool for a scanning endoscope with an insertion portion inserted therein, the calibration tool including a position adjustment mechanism and an inclination adjustment mechanism. Note that, here also, components of a calibration tool 60 for a scanning endoscope that have been described above are provided with reference numerals that are the same as those of the first and second embodiments, and a description thereof will be omitted.

As illustrated in FIG. 18, a calibration tool 60 according to the present embodiment includes a position adjustment mechanism 70 that adjusts and fixes the center position in the radial direction of the distal end portion 12 in addition to a configuration in which through holes 64*b* and 63*a* are provided at a center of a bottom portion 64 and a center of a calibration pattern on a chart 63 in a bottomed cylindrical portion 61, respectively, enabling easy alignment of the center position in the radial direction of the distal end portion 12.

The position adjustment mechanism 70 includes a knob 71, a screw portion 72 joined to the knob 71, and a block-like holding body 73 in which the screw portion 72 is pivotally disposed. As illustrated in FIG. 19, four such position adjustment mechanisms 70 are disposed in a cruciform, i.e., horizontally and vertically (in the horizontal and vertical directions indicated by X-X' and Y-Y' in the Figure) around the periphery of the bottomless cylindrical portion 62.

The screw portion 72 in each position adjustment mechanism 70 is threadably connected to a thick wall portion of the bottomless cylindrical portion 62 and is advanced/retracted in an axial direction thereof by an operation to turn the knob 71 arranged so as to project from an outer peripheral portion of the bottomless cylindrical portion 62. Also, a surface of the holding body 73, the surface facing an outer peripheral face of the distal end portion 12, is curved so as to be in surface contact with the distal end portion 12, and the holding body 73 moves following advancing/retracting movement in the axial direction of the screw portion 72.

With the calibration tool 60 configured as described above, positions of the holding bodies 73 that are in contact with the distal end portion 12 of the endoscope 2 can be adjusted to respective positions allowing illuminating light from the illumination fiber 14 to be viewed from the through hole 64*b* of the bottom portion 64 by an operation to turn the respective knobs 71 in the four position adjustment mechanisms 70. In other words, the calibration tool 60 can move and adjust the position in the radial direction of the distal end portion 12 in the X-X'/Y-Y' directions in FIG. 19 by means of the four position adjustment mechanisms 70. Note that the calibration tool 60 holds the outer peripheral portion of the distal end portion 12 via the respective holding bodies 73 of the four position adjustment mechanisms 70 to fix the position in the radial direction of the distal end portion 12 after movement and adjustment.

Note that in the calibration tool 60, an inclination adjustment mechanism 80 illustrated in FIG. 20 may be provided in addition to the four position adjustment mechanisms 70.

More specifically, the inclination adjustment mechanism 80 includes a knob 81, a screw portion 82 joined to the knob 81, a block-like moving body 83 in which the screw portion 82 is pivotally disposed, and a guide body 84 that guides the moving body 83.

The screw portion 82 in the inclination adjustment mechanism 80 is threadably connected to a thick wall portion of a bottomless cylindrical portion 62 and is advanced/retracted in an axial direction thereof by an operation to turn the knob 71 arranged so as to project from an outer peripheral portion of the bottomless cylindrical portion 62. The moving body 83 moves following advancing/retracting movement in the axial direction of the screw portion 72. The moving body 83 includes a through-hole 83*a*, which is a hole portion through which the distal end portion 12 of the endoscope 2 is inserted, and a distal end face includes a curved surface 83*b* that is a recessed spherical segment surface.

The guide body 84 is fixed inside the bottomless cylindrical portion 62, and includes a through-hole portion 84*a*, which is a hole portion through which the distal end portion 12 of the endoscope 2 is inserted. The through-hole portion 84*a* includes a tapered inner surface that is larger than an outer shape of the distal end portion 12 and has a diameter increasing toward the front. Also, a proximal end face of the guide body 84 includes a curved surface 84*b* that is a projecting spherical segment surface. The moving body 83 is provided at the rear of the guide body 84 so as to be continuous with the guide body 84 so that the curved surface 84*b* of the guide body 84 and the curved surface 83*b* of the moving body 83 are in surface contact with each other.

With the calibration tool 60 configured as described above, an inclination of the distal end portion 12 can be adjusted because the distal end portion 12 inserted through the moving body 83 is inclined along with inclining movement of the moving body 83 along the curved surface 84*b* of the guide body 84, the inclining movement being made by an operation to turn the knob 81 in the inclination adjustment mechanism 80.

Note that for the calibration tool 60 according to the present embodiment, a configuration in which a through hole 64*b* is provided at the center of the bottom portion 64 of the bottomed cylindrical portion 61 is indicated as an example, but the configuration of the calibration tool 60 is not limited to this one, and the position adjustment mechanisms 70 and the inclination adjustment mechanism 80 may be provided in a configuration including the photodetector 68 in the second embodiment.

Note that the invention for which the embodiments have been described above is not limited to the embodiments and the modifications thereof, and in the practical phase, various modifications can be made without departing the spirit of the invention. Furthermore, the above-described embodiments include inventions of various phases, and a proper combination of a plurality of elements disclosed herein enables extraction of various inventions.

For example, even if some elements are deleted from all the elements in any of the above embodiments, the resulting configuration with the element deleted can be extracted as an invention as long as such configuration can solve the problems stated herein and provides the effects stated herein.

What is claimed is:

1. A calibration tool for a scanning endoscope, provided for calibrating an image acquired by a scanning endoscope that scans illuminating light and detects return light to create an image, the calibration tool comprising:

an abutment portion that is in contact with and abuts an illumination window provided in a distal end face of an insertion portion of the scanning endoscope and is configured to be in contact with a region of the illumination window other than a region in which an illuminating light beam applied from the illumination window is scanned; and a chart with a calibration pattern drawn thereon, the calibration pattern being provided for calibrating a scan pattern of the illuminating light, the chart being arranged parallel to the distal end face with a predetermined distance from a surface of the illumination window positioned as a result of the illumination window coming into contact with the abutment portion, according to a size of the calibration pattern.

2. The calibration tool for a scanning endoscope according to claim 1, further comprising:

a bottomed cylindrical portion including a bottom portion for occluding an end portion, the bottom portion being provided on a distal end side, the chart being provided on a wall surface of the bottom portion; and a bottomless cylindrical portion including a plurality of the abutment portions provided so as to extend inward in a radial direction from an opening portion on a distal end side thereof that is threadably connected to the bottomed cylindrical portion.

3. The calibration tool for a scanning endoscope according to claim 1, wherein the calibration pattern includes a pattern that is point-symmetrical with respect to a center.

4. The calibration tool for a scanning endoscope according to claim 3, further comprising an adjustment mechanism that adjusts a distal end position of the insertion portion so that a beam axis of the illuminating light that is not scanned coincides with the center of the calibration pattern.

5. The calibration tool for a scanning endoscope according to claim 3, further comprising an adjustment mechanism that adjusts a distal end position of the insertion portion so that a center of a scan of the illuminating light that is scanned coincides with the center of the calibration pattern.

6. The calibration tool for a scanning endoscope according to claim 1, wherein the abutment portion is configured to be in contact with the illumination window positioned outside a region of a detection window provided in the distal end face without the abutment portion covering the detection window.

7. The calibration tool for a scanning endoscope according to claim 1, wherein the abutment portion is light transmissive.

* * * * *